(12) United States Patent
Robbins

(10) Patent No.: US 11,553,953 B1
(45) Date of Patent: Jan. 17, 2023

(54) BONE SCREW SYSTEM AND METHOD

(71) Applicant: Joseph T. Robbins, Vestavia Hills, AL (US)

(72) Inventor: Joseph T. Robbins, Vestavia Hills, AL (US)

( * ) Notice: Subject to any disclaimer, the term of this patent is extended or adjusted under 35 U.S.C. 154(b) by 191 days.

(21) Appl. No.: 17/017,403

(22) Filed: Sep. 10, 2020

Related U.S. Application Data

(60) Provisional application No. 62/898,311, filed on Sep. 10, 2019.

(51) Int. Cl.
*A61B 17/86* (2006.01)
*A61B 17/70* (2006.01)

(52) U.S. Cl.
CPC ........ *A61B 17/863* (2013.01); *A61B 17/7055* (2013.01); *A61B 17/8605* (2013.01); *A61B 17/8635* (2013.01)

(58) Field of Classification Search
CPC .................................................. A61B 17/863
See application file for complete search history.

(56) References Cited

U.S. PATENT DOCUMENTS

2015/0272646 A1\* 10/2015 Russell .............. A61B 17/8841
606/93
2021/0369314 A1\* 12/2021 Preiss-Bloom ....... A61L 31/148

\* cited by examiner

*Primary Examiner* — Olivia C Chang
(74) *Attorney, Agent, or Firm* — C. Brandon Browning; Maynard Cooper & Gale PC

(57) ABSTRACT

The present disclosure generally pertains to methods and systems for fusing a joint. The disclosure includes mechanically immobilizing the joint by insertion of a bone screw, the bone screw including a screw shaft operatively coupled to a screw head, the screw shaft including a longitudinal axis, a channel extending along the longitudinal axis, a first shaft wall section, a second shaft wall section and a third shaft wall section. Fusing of the joint includes inserting the screw into a first bone, a second bone and a joint formed between the first bone and the second bone. Insertion further includes cutting bone pieces away from the first bone using the third shaft wall section of the bone screw and directing the first bone pieces into a helical depression formed in the third shaft wall section.

11 Claims, 6 Drawing Sheets

BONE SCREW SYSTEM AND METHOD

RELATED APPLICATIONS

This application claims priority to U.S. Provisional Patent Application No. 62/898,311 filed on Sep. 10, 2019, titled "Bone Screw System and Method", the entire contents of which are incorporated herein by reference.

FIELD OF USE

The present invention is directed to a bone screw system and, more particularly, a bone screw configured for immobilizing the sacroiliac joint by directing autologous bone removed from the ilium and the sacrum as the bone screw passes therethrough into a helical depression of the screw and out therefrom into either a screw shaft central channel for promoting bony growth through the screw shaft or the sacroiliac joint where the autologous bone is directed radially outward from the screw shaft by a tapered, threadless shaft sidewall for increasing the surface areas of the ilium and sacrum between which fusion occurs.

BACKGROUND OF INVENTION

Immobilization of a joint may be desirable in instances where disorders or injury to the joint results in degeneration, fracture or instability and causes significant pain. An exemplary joint is the sacroiliac joint, which is located between the sacrum and the ilium bones. Sacroiliac joint pain may be felt in the lower back, buttocks, groin, pelvis, and legs of individuals suffering from trauma, stress, or disorders of the sacroiliac joint.

Non-surgical treatments to address symptoms associated with sacroiliac joint injuries or disorders may include the administration of steroids, pain medication, radiofrequency neurotomy rehabilitation, exercise and complementary medicine. However, these potential treatments may provide only temporary relief or reduction of pain associated with the sacroiliac joint. Surgical treatment can offer a more permanent approach to pain management and relief and may utilize hardware, such as a bone screw, to immobilize the joint.

A bone screw is often a metal implant that may be inserted through a first bone, across the joint to be immobilized, and into a second bone. In the instance where the joint is the sacroiliac joint, a bone screw may be inserted into the ilium, across the sacroiliac joint, and into the sacrum. Further, portions of bone that are cut away from the first bone as the bone screw is inserted may be collected within the bone screw and utilized to encourage bone growth and fusion of the joint. The present disclosure describes joint immobilization systems and methods that may both immobilize the joint and aid in the bone growth and joint fusion process after insertion across the joint.

SUMMARY OF THE INVENTION

The present invention is directed to methods and systems for treating pain by stabilizing and fusing the sacroiliac joint. The fusing may occur mechanically by providing an insert through an ilium bone, across the sacroiliac joint, and into a sacrum bone. According to one aspect of the invention, there is provided a bone screw including a screw head and a screw shaft operatively coupled to the screw head. The screw shaft may include a channel extending along a longitudinal axis of the shaft. The channel may extend completely through the shaft and each end thereof or only through a portion of the shaft, for example, the channel may extend within the shaft only along the length of the shaft that is intended for engagement with ilium, the sacrum, the joint space or any combination thereof.

The shaft may also include three distinct sections, namely, a first shaft wall section, a second shaft wall section and a third shaft wall section, where the second shaft wall section is located between the first shaft wall section and the third shaft wall section. The first shaft wall section may be threaded and include a first length and a first constant outer core diameter. The second shaft wall section may be threadless and substantially smooth and include a second length and at least one opening extending to and between the channel and an exterior of the second shaft wall section, the second shaft wall section tapering inwardly along the second length towards the longitudinal axis as its extends from the first shaft wall section towards the third shaft wall section. The third shaft wall section may be threaded and include a third length, a third constant outer core diameter, at least one exterior helical depression formed in the third shaft wall section and at least hole extending to and between the channel and at least one helical depression.

At the distal end of the third shaft section a self-tapping, thread-cutting distal tip portion may be provided for promoting the initial insertion of the screw into the ilium and the sacrum. The at least one helical depression may extend to and between the self-tapping distal tip portion and the second shaft wall section for directing the autologous bone through a hole in the depression and into the channel of the shaft. Additionally, the first outer diameter of the first shaft wall section may be about 3 mm greater than the third outer diameter of the third shaft wall section. Additionally, the channel of the bone screw may include an inner channel wall and at least one inner helical depression formed in the inner channel wall for promoting movement of bone in the channel proximally.

The screw shaft of the bone screw may include a continuous shaft wall step extending to and between and formed by the intersection of the first shaft wall section and the second shaft wall section, the continuous shaft wall step being configured for preventing movement of bone pieces removed from the ilium and/or sacrum proximally along the screw shaft as it advances through the bone and sacroiliac joint. For example, bone pieces directed proximally along the at one depression and into a void defined between the second shaft wall section and either bone or joint may be prevented from moving proximally out of the void by the continuous shaft wall step, which forms a barrier.

The bone screw may also include a load distribution cap pivotally and rotatably seated on the screw head for promoting secure attachment of the screw head to the exterior of the ilium regardless of the angle of insertion of the screw into the bone. The screw head may include a head step at a proximal end of the screw head and at least one pair of flattened regions extending from the head step toward a distal end of the screw head that provides indentions in a semi-spherical region of the screw head. The at least one pair of flattened regions may be located approximately 180 degrees about a circumference of the screw head from each other. The head step, the at least one pair of flattened regions and indentations allow the cap to be operatively coupled to the screw head.

According to yet another aspect of the invention, there is provided a method of fusing a joint including inserting a screw into an ilium, a sacrum and a joint formed between the ilium and the sacrum, the screw including a central channel, a first section at a proximal end of the screw, a second section having an opening extending into the channel and a third section at a distal end of the screw. Sacrum bone pieces are cut away from the sacrum using the third section and directed into a helical depression formed in the third section where a first portion of the sacrum bone pieces is directed through a first hole in the helical depression and into a central channel of the screw, a second portion of the sacrum bone pieces is directed into the opening in the second section and a third portion of the sacrum bone pieces is directed into the joint. Ilium bone pieces are cut away from the ilium using the second section and a first portion of the ilium bone pieces is directed into the opening in the second section and a second portion of the ilium bone pieces is directed into the joint. Additional ilium bone pieces are cut away from the ilium using a continuous cutting edge formed by an intersection of the first section and the second section where a first portion of the additional ilium bone pieces is directed into the opening in the second section and a second portion of the additional ilium bone pieces is directed into the joint. The second section includes a sidewall that tapers towards the distal end that directs the third portion of the sacrum bone pieces, the second portion of the ilium bone pieces and the second portion of the additional ilium bone pieces radially outward from the screw.

In one embodiment, the method includes drilling a hole through the ilium having a diameter that is greater than a diameter of the third section and less than a diameter of a core diameter of the first section. The diameter of the hole is increased to a second diameter by the cutting of the ilium bone pieces away from the ilium using the second section and the second diameter is increased to a third diameter by the cutting of the additional ilium bone pieces away from the ilium using the continuous cutting edge formed by the intersection of the first section and the second section. This occurs without third section cutting away bone from the ilium.

In another embodiment, the joint is distracted by the movement of the third portion of the sacrum bone pieces, the second portion of the ilium bone pieces and the second portion of the additional ilium bone pieces into the joint. In another embodiment, the sidewall of the second section may direct the third portion of the sacrum bone pieces, the second portion of the ilium bone pieces and the second portion of the additional ilium bone pieces radially outward 360 degrees from the screw. In yet another embodiment, the method includes operatively coupling a cap to the proximal end of the screw by inserting the third section, the second section and the first section through an opening in the cap and pressing the cap onto a screw head forming the proximal end of the screw.

A further understanding of the nature and advantages of the present invention will be realized by reference to the remaining portions of the specification and the drawings.

BRIEF DESCRIPTION OF DRAWINGS

The sacroiliac bone screw system and method of the present invention can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION OF THE INVENTION

Figure 1:
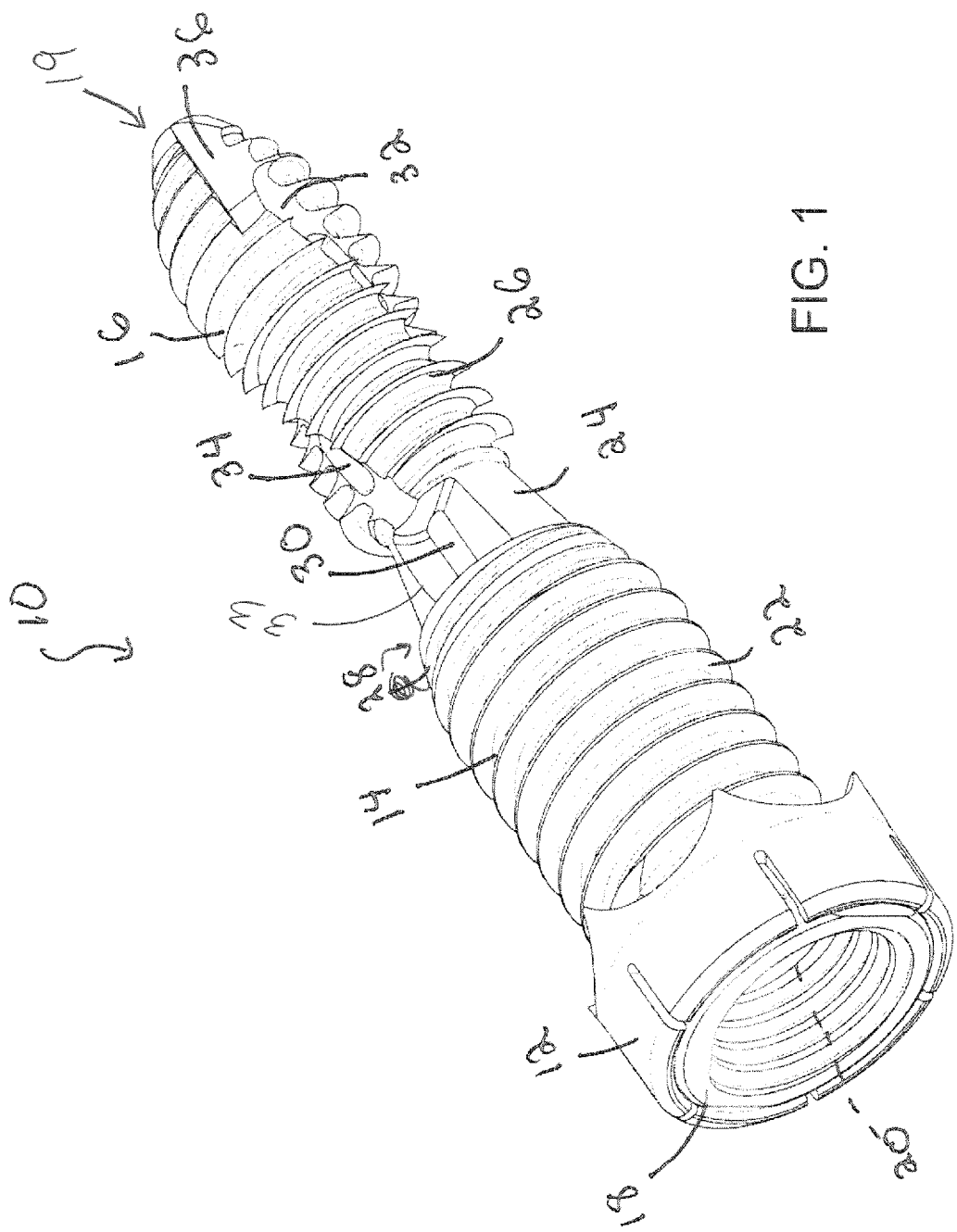
FIG. 1 is a perspective view of a bone screw system including a cap and a bone screw in accordance with a first embodiment of the present invention.

The present invention is generally directed to bone screw systems and methods of using same for joint immobilization. More particularly, the present invention is directed to a sacroiliac bone screw system 10 and method of using same for fusing together an ilium 11 and a sacrum 13 of a sacroiliac joint 15, the method generally including inserting a bone screw 14 into ilium 11, sacrum 13 and joint 15 and cutting bone pieces away from the ilium and the sacrum using cutting edges of the bone screw as the screw advances through the bones. Bone screw 14 is configured for utilizing essentially all of the cut away bone pieces in the immobilization of the joint 15. This is accomplished by limiting the amount of bone pieces escaping from the joint area as the screw advanced through the bones and joint and directing the bone pieces to those places within the joint area best suited for causing and promoting effective immobilization of the joint 15. Thus, a portion of the bone pieces are collected and stored within bone screw 14 for encouraging bone growth into, through and out of the bone screw, while another portion of the bone pieces are directed into joint 15 and radially outward from bone screw 14 for promoting bone growth to and between the ilium and the sacrum. By directing a portion of the bone pieces radially outward from bone screw 14 and into joint 15, the surface areas of the ilium and the sacrum that are directly fused together across the joint are greater than what is provided by conventional bone screws. The ability of bone screw system 10 to more effectively fuse adjacent bones across a joint than conventional bone screws results from the configuration of bone screw 14, as illustrated in FIGS. 1 through 7 and explained below in detail.

FIGS. 1 through 7 of the application depict bone screw system 10, where like features share like reference numerals. FIG. 8 of the application depicts bone screw system 10 fully engaged with an ilium and a sacrum of a sacroiliac joint. It should be noted that all terms as used herein are given their common meaning as known in the art and as further described and discussed hereafter. As used herein, the singular forms "a", "an", and "the" include plural referents unless the context clearly indicates otherwise.

Figure 2:
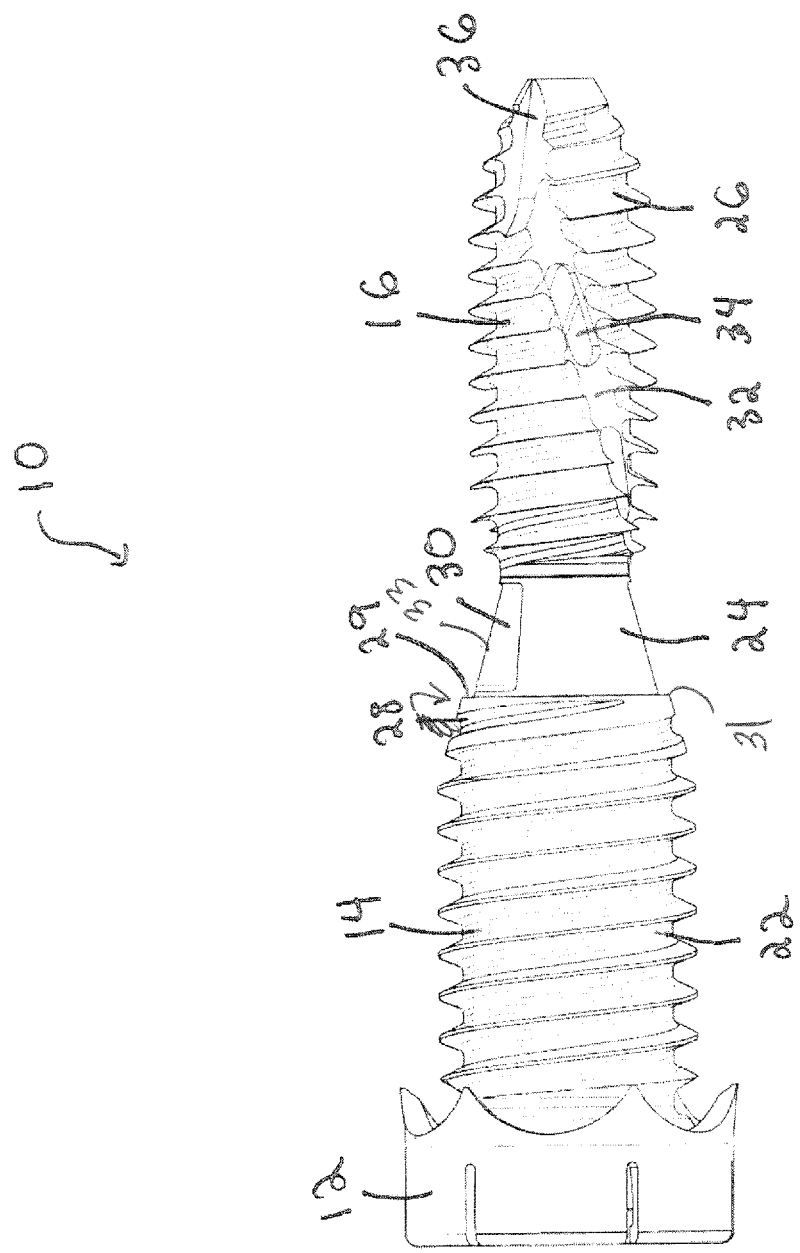
FIG. 2 is an elevational view of the bone screw system of FIG. 1.
Figure 3:
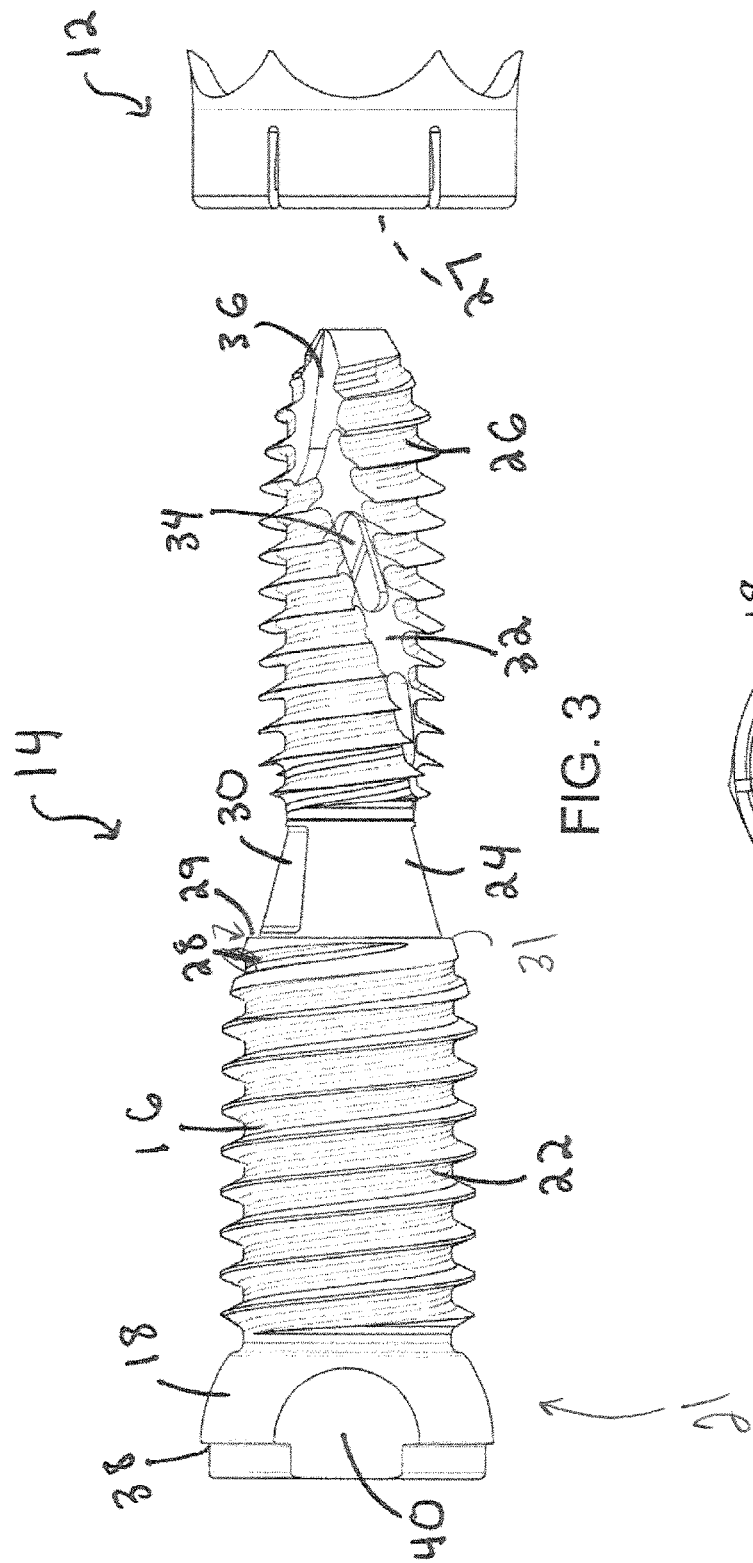
FIG. 3 is an elevational view of the bone screw system of FIG. 1 disassembled.
Figure 4:
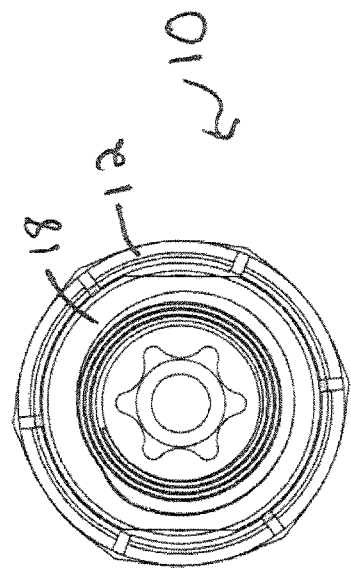
FIG. 4 is a plan view of a proximal end of the bone screw of FIG. 1.
Figure 5:
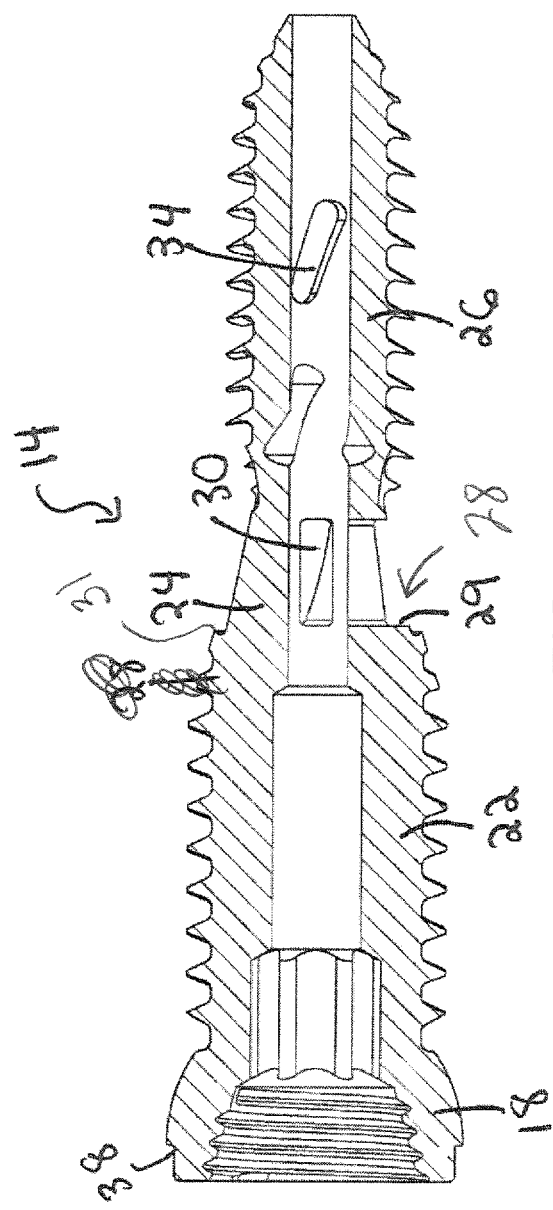
FIG. 5 is a sectional view the bone screw of FIG. 3.
Figure 6:
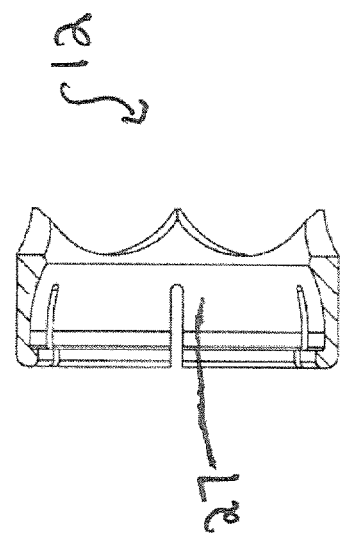
FIG. 6 is a sectional view of the cap of FIG. 3.

Referring to FIGS. 1 and 2, bone screw system 10 includes a cap 12, as further described hereafter, rotatably and pivotally, i.e., conically rotatably, coupled to a screw head 18 of a bone screw 14. Bone screw 14 is fabricated from a metal such as titanium and includes an integrally formed screw shaft 16 extending distally therefrom. Shaft 16 is formed by an elongate continuous sidewall that defines a longitudinal axis extending centrally through screw head 18 and a distal tip 19 of the screw. The sidewall defines a hollow channel 20 that extends within shaft 16 along the longitudinal axis and out through screw head 18 and the distal tip of the screw. Channel 20 is arranged to receive and store bone pieces cut away from bone as bone screw 10 advances therethrough when rotated.

The sidewall of shaft 16 includes three distinct sections, namely, a first shaft wall section 22, a second shaft wall section 24 and a third shaft wall section 26 with the second shaft wall section being located between first shaft wall section 22 and third shaft wall section 26. Shaft wall sections 22, 24 and 26 are identified by differing wall features, lengths, and diameters. In particular, first shaft wall section 22 is located at a proximal end 21 of bone screw 10 and directly coupled with screw head 18. First shaft wall section 22 includes a length of 20 mm to 26 mm, a constant core diameter and cortical threads, and more particularly, aggressive, double lead cortical threads. The constant core diameter is measured between opposing valleys or troughs formed by the cortical threads. Third shaft wall section 26 is located at a distal end of bone screw 10 and includes a constant core diameter that is less than the core diameter of the first shaft wall section 22 and cancellous threads, and more particularly aggressive, double lead cancellous threads. The length of third wall section 26 may vary depending on the size of the patient. The cancellous screw threads of third shaft wall section 26 are larger and have a higher pitch in comparison to the cortical screw threads of section 22. The core diameter of first shaft wall section 22 is 3 mm greater than the core diameter of third shaft wall section 26. This is required to ensure that second shaft wall section 24 includes the desired ramp or taper, as further described herein. Exemplary first shaft wall 22 and third shaft wall 26 diameters include 13 mm and 10 mm, 12 mm and 9 mm, 11 mm and 8 mm and 10 mmm and 7 mm, respectively. The length of first shaft wall section 22 may be greater than, approximately equal to, or less than the length of third shaft wall section 26. The locations and types of threads in sections 22 and 26 act to create joint compression as the screw passes through the sacrum. Additionally, threaded sections 22 and 26 of screw shaft 16 include tapered inner diameter threads that aid in wobble prevention during bone screw 14 placement.

Unlike shaft wall sections 22 and 26, second shaft wall section is not configured to form threads within bone, either by cutting the bone or plastic deformation of the bone. As such, second shaft wall section 24 is threadless and is formed by a substantially smooth sidewall. The length of the sidewall, extending to and between first shaft wall section 22 and third shaft wall section 26, is less than the length of section 22 and less than the length of section 26, and may be sized to approximately match the width of the standard joint space anatomy or the joint space of the joint into which bone screw 14 is to be placed. The sidewall forming second shaft wall section 22 is tapered inwardly to form a ramp along its length towards the longitudinal axis of shaft 16 as it extends from first shaft wall section 22 towards third shaft wall section 26. The taper of second shaft wall section 24 towards the distal end of bone screw 10 serves to direct bone pieces radially outward from bone screw 10 and into the joint during insertion and advancement of second shaft wall section into the joint space and compression of the joint.

Within the sidewall forming second shaft wall section 24 are two opposed openings 30 extending to and between channel 20 and an exterior of second shaft wall section 24. Openings 30 may be in the shape of an oval, a rounded quadrilateral, or any other shape suitable for cutting and collecting bone material within bone screw 10 and providing a pathway through which bony fusion may occur. Opening 30 is tapered consistent with the tapering of second shaft wall section 24 and under-cut with a cutting edge for self-harvesting bone material in the joint space during bone screw 10 insertion through ilium 11. Openings 30 may become fully filled with bone material after insertion of bone screw 10 into the joint. Although, two openings 30 are shown, it is contemplated that the second shaft wall section 24 may include one opening or up to four openings.

Located between and distinguishing first shaft wall section 22 from second shaft wall section 24 is a continuous shaft wall step 28 shoulder. Shaft wall step 28 is formed by an annular wall 29 that intersects section 22 to form a continuous cutting edge 31 and extends to and intersects with second shaft wall section 24. Annular wall 29 has a constant radial width that is equal to the difference between the diameter of section 22 and the diameter of section 24 along their respective intersections with radial wall 29. Continuous shaft wall step 28 forms an undercut portion that allows the capture and packing of loose bone material as the screw is rotated and advances distally through the ilium thereby creating a seal over the joint space. Such loose bone material may include bone pieces removed by cutting edge 31 from the ilium and/or bone pieces removed from the sacrum by the cancellous threads for third shaft wall section 26.

Third shaft wall section 26 includes a pair of opposed helical depressions 32 that are formed in the exterior of the sidewall of third shaft wall section 26. Depressions 32 extends to and between a self-tapping tip of shaft 16, as described hereafter, and the proximal-most edge of third shaft wall section 26. The proximal-most edge of each depression 32 is aligned with one of openings 30 in second shaft wall section 24 so that bone pieces removed from sacrum 13 within the depressions are directed proximally toward and into openings 30. Each depression includes a pair of holes 34 extending to and between channel 20 and the exterior surface of the depressions. The helical patterns of helical depressions 32 each has a 45 degree helix angle with two hooked under-cut flutes that allow for bone shear, harvesting, and drawing of bone material from sacrum 15 into channel 20 and directing bone proximally. Each of holes 34 may be in the shape of an oval, a rounded quadrilateral, or any other shape suitable for harvesting and collecting bone material within bone screw 10. Third shaft wall section 26 also includes a self-tapping, cutting-type distal tip portion 36 to initiate bone engagement as bone screw 10 begins insertion into sacrum 13.

Referring to FIGS. 3 through 6, screw head 18 includes a semi-spherical region and a head step 38 at a proximal end of screw head 18. A pair of flattened regions 40 extends from head step 38 toward a distal end of screw head 18 and provides indentations in the semi-spherical region of screw head 18. Respective flattened regions 40 are located approximately 180 degrees about a circumference of screw head 18 from each other and create access surfaces for a screw removal tool. Cap 12 is slotted to flex and permanently lock over screw head 18 and includes flared teeth that may sink into bone, such that cap 12 is compressed to screw head 18. Cap 12 is seated onto screw head 18 by inserting sections 22, 24 and 26 through a central opening 27 in cap 12 and flexing the cap over the screw head thereby locking the cap in place on the screw head. Cap 12 is capable of being pivotally and rotatably seated on screw head 18, where the semi-spherical region aids in cap 12 conical rotation and uniform load distribution and head step 38 allows for cap 12 assembly, controlled conical rotation and locking. Bone screw 10 may optionally be assembled in the surgical theatre. The assembled cap 12 and screw body 14 form bone screw system 10. Specifically referring to FIGS. 4 the 5, bone screw 10 includes an interface for a hexalobe driver inserted through the proximal end of bone screw 10, as well as inserter locking threads within screw head 18.

Figure 7:
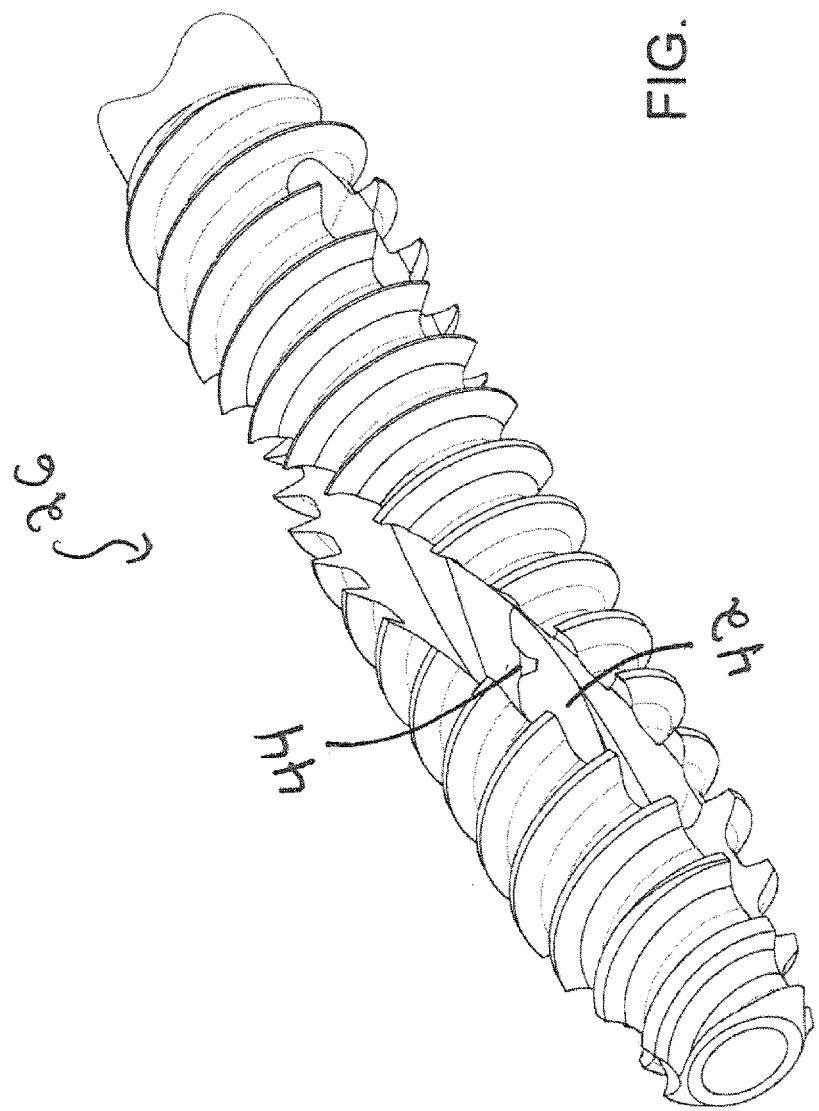
FIG. 7 is a perspective view of a third shaft wall section of the bone screw of FIG. 1.
Figure 8:
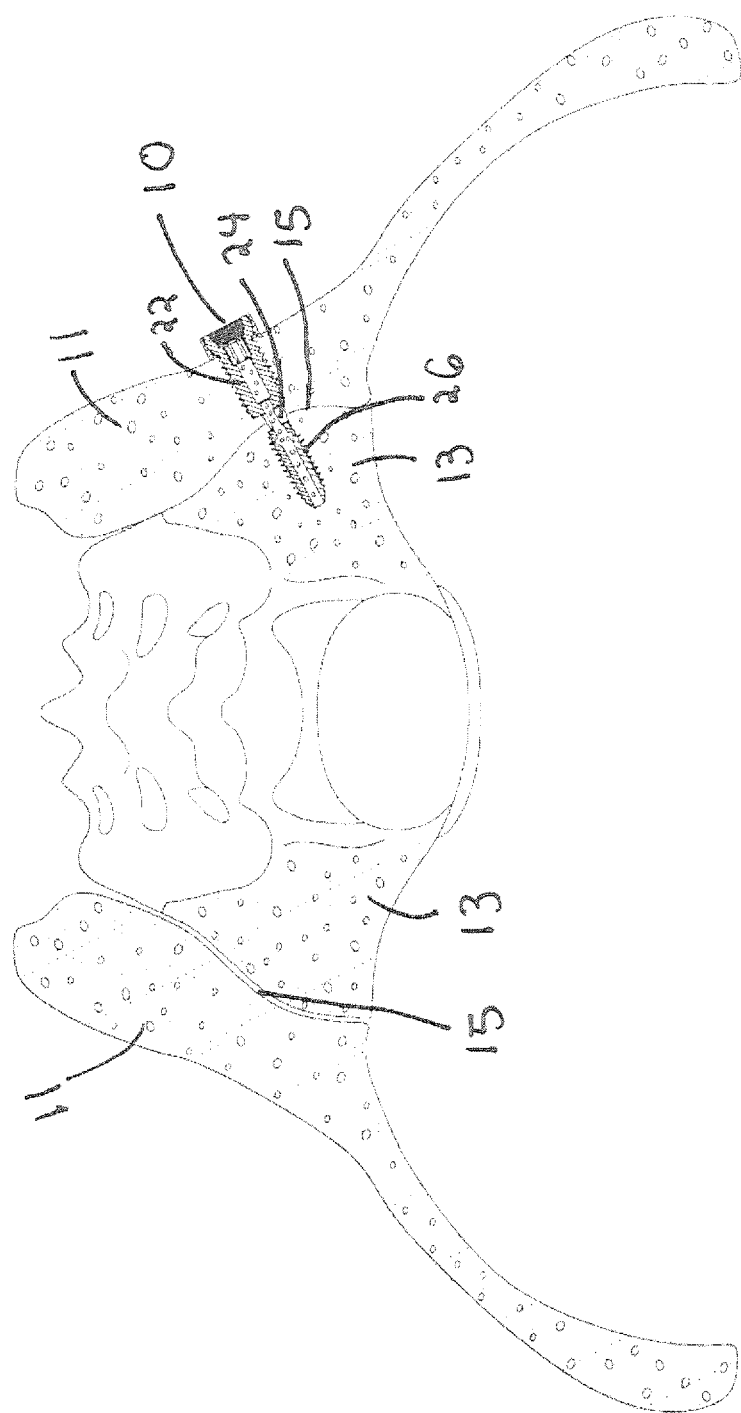
FIG. 8 is a partial sectional view of a sacroiliac joint illustrating the bone screw of FIG. 1 inserted into an ilium bone, spanning the sacroiliac joint, and entering a sacrum bone.

Referring to FIG. 7, channel 20 in third shaft wall section 26 includes an inner channel wall 42 and at least one inner helical depression 44 formed in inner channel wall 42. Inner helical depression 44 is provided for promoting movement of the bone pieces proximally within the channel.

Bone screw system 10 is utilized in a method for fusing the sacroiliac joint. Referring to FIG. 8, the method includes creating an incision in a patient's skin adjacent to the ilium. A drill is used to create an pathway through ilium 11, into sacroiliac joint 15 and a short distance into sacrum 13 using a drill bit having a diameter that is greater than the diameter of third shaft wall section 26 and less than the constant core diameter of first shaft wall section 22. The diameter of the drill bit and thus the hole drilled by the drill bit is greater than the average diameter of second shaft wall section 24 and less than the diameter of the intersection of annular wall 29 and second shaft wall section 24. So not to disturb cancellous bone of the sacrum, the pathway drilled into the sacrum has a length of about 5 mm or less and extends only into cortical bone of the sacrum.

After a hole is drilled through ilium 11, joint 15 and sacrum 13, distal tip portion 36 of third shaft wall section 26 of screw 14 is inserted into the pathway and passed into and through ilium 11 without the removal of bone from the ilium by the third shaft wall section 26 since the diameter of the hole is greater than the diameter of third shaft wall section 26. Distal tip portion 36 then engages sacrum 13, and screw 14 is rotated thereby causing the advancement of screw 14.

Similar to third shaft wall section 26, the distal end of second shaft wall section 24 also passes through the hole in ilium 11 without the need to cut away bone of the ilium since it has a diameter that is less than the diameter of the hole; however, as second shaft wall section continues forward through the ilium, that portion of the tapered sidewall of second wall section 24 having a diameter equal to the diameter of the hole comes into contact with an exterior surface of the ilium. When that occurs a cutting edge 33 of each opening 30 engages the exterior surface of the ilium, and as screw 14 is rotated, being pulled along by the engagement of third shaft wall section 26 with sacrum 13, cutting edge 33 begins to remove bone pieces from ilium 11 thereby progressively widening the hole as the tapered sidewall of second shaft wall section 24 advances through ilium 11. A portion of the bone piece is directed through openings 30 and into channel 20.

Eventually shaft wall step 28 engages the exterior surface of ilium 11. When that occurs, continuous cutting edge 31 begins to shave away additional bone pieces away from ilium 11 thereby widening the hole and extends to and intersects with second shaft wall section 24. The bone pieces removed by cutting edges 31 and 33 are pressed distally towards joint 15. That is, Annular wall 29 acts to prevent proximal migration of bone pieces cut away from ilium 11 by first and second shaft wall section 22 and 24.

As screw 14 progresses farther into joint 15, the cancellous threads of third shaft wall section 26 cut away bone pieces from sacrum 13. As the sacrum bone pieces are cut away, the pieces are directed by helical depression 32 into holes 34 and ultimately into channel 20. As bone pieces begin to amass within channel 20, the movement of new bone pieces into the channel, which is driven in part by the configurations of the threads, as described above, forces the sacrum bone pieces proximally within channel 20, thereby packing the bone pieces in the channel. Other portions of the sacrum bone pieces are directed via depressions 32 into openings 30 of second shaft wall section 24. Still other sacrum bone pieces, which are prevented from proximal migration out of joint 15 by continuous step 28, are directed into joint space 15 where they accumulate about screw shaft 16 and are pressed radially outward as the tapered sidewall of second shaft sidewall section 24 passes into the joint space. As ilium bone pieces are pressed distally into joint 15 and sacrum bone pieces are pressed proximally into joint 15, joint 15 is temporarily distracted by the mass of bone pieces being compressed into the joint. By preventing proximal movement of the bone pieces, as described above using continuous step, the amount of sacrum and ilium bone pieces packed into channel 20 and joint space 15 is maximized, which means the amount of bone pieces directed radially outward by second shaft wall section 24 is increased such that the surface area of the ilium and the sacrum within the joint space that in in contact with the bone pieces is maximized, which in turn, results in increased volume of bony growth and fusion across the joint. As bone screw 14 progresses, the action of the cancellous threads and the cortical threads causes compression across the joint. When fully engaged with and inserted into the ilium, sacrum and joint, screw 14 comes to rest with a proximal portion of second shaft wall section 24 spanning the joint.

As will be understood by those familiar with the art, the present invention may be embodied in other specific forms without departing from the spirit or essential characteristics thereof. For example, it is contemplated that to immobilize a sacroiliac joint, up to three bone screws 14 may be used having varying lengths and diameters. Accordingly, the disclosures and descriptions herein are intended to be illustrative, but not limiting, of the scope of the invention which is set forth in the following claims.

I claim:

1. A bone screw comprising:
   a screw shaft including a longitudinal axis, a channel extending along the longitudinal axis, a first shaft wall section, a second shaft wall section and a third shaft wall section, the second shaft wall section being located between the first shaft wall section and the third shaft wall section, and
   a screw head and a cap pivotally and rotatably seated on the screw head,
   wherein the first shaft wall section is threaded,
   wherein the second shaft wall section includes at least one opening extending to and between the channel and an exterior of the second shaft wall section, the second shaft wall section tapering inwardly towards the longitudinal axis as it extends from the first shaft wall section towards the third shaft wall section, and
   wherein the third shaft wall section is threaded and includes at least one exterior helical depression formed in the third shaft wall section and at least one hole extending to and between the channel and the at least one helical depression.

2. The bone screw of claim 1 including a continuous shaft wall step extending to and between the first shaft wall section and the second shaft wall section.

3. The bone screw of claim 1 including a self-tapping distal tip portion.

4. The bone screw of claim 3 wherein the at least one helical depression extends to and between the self-tapping distal tip portion and a proximal end of the third shaft wall section.

5. The bone screw of claim 1 wherein the first shaft wall section has a first outer diameter that is about 3 mm greater than a third outer diameter of the third shaft wall section.

6. The bone screw of claim 1 wherein the channel includes an inner channel wall and at least one inner helical depression formed in the inner channel wall.

7. The bone screw of claim 1 wherein the second shaft wall section is threadless.

8. A bone screw comprising:
- a screw shaft with a channel extending along a longitudinal axis thereof, the screw shaft including a first shaft wall section that is threaded, a second shaft wall section that is not threaded and a third shaft wall section that is threaded, the second shaft wall section being located between the first shaft wall section and the third shaft wall section, and
- a screw head and a cap pivotally and rotatably seated on the screw head, the cap including acutely pointed projections configured for piercing bone,
- wherein the second shaft wall section includes at least one opening extending to and between the channel and an exterior of the second shaft wall section, the second shaft wall section tapering inwardly towards the longitudinal axis as it extends away from the first shaft wall section towards the third shaft wall section, and
- wherein the third shaft wall section is threaded and includes at least one exterior helical depression formed in the third shaft wall section and at least one hole extending to and between the channel and at least one helical depression.

9. The bone screw of claim 8 wherein the screw head includes a head step at a proximal end of the screw head.

10. The bone screw of claim 9 wherein at least one pair of flattened regions extends from the head step toward a distal end of the screw head and provides indentions in a semi-spherical region of the screw head.

11. The bone screw of claim 10 wherein the at least one pair of flattened regions are located approximately 180 degrees about a circumference of the screw head from each other.

* * * * *